(12) United States Patent
Eliaz

(10) Patent No.: US 12,673,146 B2
(45) Date of Patent: *\*Jul. 7, 2026*

(54) PLASMAPHERESIS DEVICE

(71) Applicant: ELIAZ THERAPEUTICS, INC.,
Sebastopol, CA (US)

(72) Inventor: Isaac Eliaz, Santa Rosa, CA (US)

(73) Assignee: ELIAZ THERAPEUTIC, INC.,
Sebastopol, CA (US)

( * ) Notice: Subject to any disclaimer, the term of this
patent is extended or adjusted under 35
U.S.C. 154(b) by 1149 days.

This patent is subject to a terminal dis-
claimer.

(21) Appl. No.: 17/146,161

(22) Filed: Jan. 11, 2021

(65) Prior Publication Data

US 2021/0138143 A1     May 13, 2021

Related U.S. Application Data

(60) Division of application No. 15/104,302, filed as
application No. PCT/US2014/038694 on May 20,
(Continued)

(51) Int. Cl.
*A61M 1/34* (2006.01)
*A61M 1/36* (2006.01)

(52) U.S. Cl.
CPC ........ *A61M 1/3496* (2013.01); *A61M 1/3403*
(2014.02); *A61M 1/3472* (2013.01);
(Continued)

(58) Field of Classification Search
CPC . A61M 1/3496; A61M 1/3486; A61M 1/3679
See application file for complete search history.

(56) References Cited

U.S. PATENT DOCUMENTS 4,172,071  A  *  10/1979  De Maeyer .......... C07K 14/565
                                                424/85.4
4,384,954  A  *   5/1983  Nakashima .......... B01J 20/3276
                                                210/287
(Continued)

FOREIGN PATENT DOCUMENTS

WO      WO-8707531  A1 *  12/1987  ............ B01J 20/321
WO      WO-9101808     *   2/1991
(Continued)

OTHER PUBLICATIONS

"Selective." Concise Oxford English Dictionary, 11th ed., rev.;
Oxford, 2008. (Year: 2008).*

*Primary Examiner* — Ariana Zimbouski
(74) *Attorney, Agent, or Firm* — The Kelber Law Group;
Steven B. Kelber

(57) ABSTRACT

A plasmapheresis device includes a column or other flow
mechanism in which plasma lows following separation of
the plasma from cellular components like blood cells, plate-
lets and the like. The column includes a moiety, such as an
antibody, which selectively binds to galectin-3. By removing
galectin-3 from the blood stream of a mammal by at least
10%, improvements in the treatment of inflammation, sup-
pression of the formation of fibroses, and a variety of cancer
treatments can be effected or improved. The device provides
tor multiple columns to remove a variety of elements but
includes one which selectively removes galectin-3 from the
blood flow. Other agents may be added to the plasma before
recombination with the cellular components of the blood,
and before returning the recombined flow to the patient.

1 Claim, 3 Drawing Sheets

Related U.S. Application Data 2014, now Pat. No. 10,953,148, which is a continuation-in-part of application No. 14/141,509, filed on Dec. 27, 2013, now Pat. No. 9,549,953.

(52) U.S. Cl.
CPC ........ *A61M 1/3486* (2014.02); *A61M 1/3672* (2013.01); *A61M 1/3679* (2013.01); *A61M 1/3693* (2013.01); *A61M 1/3696* (2014.02); *A61M 2202/0445* (2013.01); *A61M 2202/09* (2013.01); *A61M 2230/005* (2013.01); *A61M 2230/04* (2013.01); *A61M 2230/06* (2013.01); *A61M 2230/205* (2013.01); *A61M 2230/30* (2013.01)

(56) References Cited

U.S. PATENT DOCUMENTS

| | | | | |
|---|---|---|---|---|
| 4,576,928 A * | 3/1986 | Tani | ........................ | B01J 20/327 |
| | | | | 502/400 |
| 4,605,394 A * | 8/1986 | Skurkovich | ......... | A61M 1/3679 |
| | | | | 604/4.01 |
| 5,782,792 A * | 7/1998 | Jones | .................. | A61M 1/3472 |
| | | | | 424/529 |
| 6,245,038 B1 * | 6/2001 | Borberg | .............. | A61M 1/3472 |
| | | | | 604/4.01 |
| 2002/0198487 A1 * | 12/2002 | Brady | .................... | B01D 15/00 |
| | | | | 604/27 |
| 2005/0265996 A1 * | 12/2005 | Lentz | ...................... | A61P 37/02 |
| | | | | 424/143.1 |
| 2006/0129082 A1 * | 6/2006 | Rozga | ................. | A61M 1/3472 |
| | | | | 604/6.04 |
| 2009/0196938 A1 * | 8/2009 | Vogt | ..................... | B01J 20/3221 |
| | | | | 424/537 |
| 2010/0217173 A1 * | 8/2010 | Hyde | .................. | A61M 1/3687 |
| | | | | 604/5.01 |
| 2011/0280825 A1 * | 11/2011 | Karumanchi | ............. | A61P 9/12 |
| | | | | 514/59 |
| 2012/0323158 A1 * | 12/2012 | Tebbey | ................. | A61M 1/362 |
| | | | | 604/6.01 |

FOREIGN PATENT DOCUMENTS

| | | | | | |
|---|---|---|---|---|---|
| WO | WO-9616666 A1 * | 6/1996 | ............. | A61K 35/14 |
| WO | WO-2012163544 A1 * | 12/2012 | .......... | A61M 1/3472 |
| WO | WO-2013085604 A1 * | 6/2013 | ............. | A61K 35/16 |
| WO | WO-2013172966 A1 * | 11/2013 | ............. | A61L 29/06 |
| WO | WO-2013179143 A2 * | 12/2013 | .......... | A61M 1/3472 |

* cited by examiner

PLASMAPHERESIS DEVICE

This application is a divisional application of application Ser. No. 15/104,302 filed Aug. 3, 2016, now allowed, which is a National Stage Application of PCT application PCT/US2014/038694 filed May 20, 2014 which claims benefit of priority of the filing date of U.S. patent application Ser. No. 14/141,509 filed Dec. 27, 2013 the disclosure of which is incorporated herein by its entirety.

BACKGROUND

Field of the Invention

This invention is directed to devices to perform apheresis of mammalian blood, including the selective removal of some percentage of circulating galectin-3 (gal-3) from the blood. The device has the capability to not only remove galectin-3 (or other galectins) from the blood, but other potentially harmful factors, and introduce to the blood additional factors that are therapeutic or beneficial on return of the blood to the mammalian patient.

Background of the Invention

Galectin-3 has become the focus of a variety of studies looking to explain mechanisms giving rise to inflammation, fibroses and various forms of cancer in mammals. By "mammals" in this application applicant intends to describe humans, of course, but also mammals of sufficient value worth investing in their health, including companion mammals like dogs and cats, and commercial mammals, like cows, horses, goats and pigs. Higher order mammals such as monkeys, which may serve as research models as well as companion animals are also included with this term. The invention of course focuses on humans.

Galectins are a family of lectins (sugar binding proteins) that are characterized by having at least one carbohydrate recognition domain (CRD) with an affinity for beta-galactosides. These proteins were recognized as a family only recently, but are found throughout the animal kingdom, and are found in mammals, birds, amphibians, fish, sponges, nematodes and even fungi.

Galectins mediate and modulate a wide variety of intracellular and extracellular functions, and thus are both expressed within the cell and frequently targeted to a specific cytosolic site, and secreted from the cell, for distribution extra-cellularly, as a component of human plasma. Among the many functions that are mediated by extracellular galectins are inflammation, fibrosis formation, cell adhesion, cell proliferation, metastatic formation, angiogenesis (cancer) and immunosuppression.

Galectins are a family of fifteen (15) carbohydrate-binding proteins (lectins) highly conserved throughout animal species. Most galectins are widely distributed, though galectin-5, -10 and -12 show tissue-specific distribution. While galectins are variably expressed by all immune cells, they are upregulated in activated B and T cells, inflammatory macrophages, natural killer (NK) cells, and FoxP3 regulatory T cells. Galectins contain a variety of structural arrangements, but a relatively conserved carbohydrate recognition domain (CRD). The majority of galectins display a single CRD, and are biologically active as monomers (galectin-5, -7 and -10), or require homodimerization for functional activity (galectin-1, -2, -11, -13, -14 and -15). Alternatively, tandem-repeat-type galectins (galectin-4, -8, -9, and -12) contain two CRDs separated by a short linker peptide, while galectin-3 (chimeric type) has a single CRD fused to a non-lectin domain that can be complexed with other galectin-3 monomers to form an oligomeric pentamer. Of note, some galectins, such as galectin-10, bind to mannose-containing glycans. Among the family of galectins, -1, -3, and -9 are particularly important as potential therapeutic targets, and -2, -4, -5, -6, -7, -8, -10, -11, -12, -13, -14, and -15 also appear implicated in a variety of biological pathways associated with morbidity and mortality.

Thus, galectin-7 has been implicated in the development of certain forms of cancer. St. Pierre et al. *Front. Biosci.*, 1:17, 438-50 (2012) and in a variety of specific cancers, including gal-2, -4 and -8 in the context of colon and breast cancer, Barrow et al, *Clin. Cancer Res.*, 15; 17 (22) 7035-46 (2011). Squamous cell carcinoma of the tongue, Alves et al, *Pathol. Res. Pract.* 15; 207 (4) 236-40 (2011) has been shown to be associated with elevated levels of gal-1, -3 and -7, while cervical squamous carcinoma has been shown linked to gal-7 levels, Zhu et al, *Int. J. Cancer*, (August, 2012). A number of galectins, including gal-15, gal-13 and gal-10 have been demonstrated to be linked to implantation and pregnancy concerns. See, e.g., Than et al, *Eur. J. Biochem.* 271(6) 1065-78 (2004), Lewis et al, *Biol. Reprod.* 77(6); 1027-36 (2007). A number of galectins, including gal-2, 3, 8 and others have been identified as correlating with various autoimmune disorders, such as lupus. Salwati et al, *J. Infect. Dis.* 1; 202(1) 117-24 (2010), Pal et al, *Biochim. Biophys. Acta.*, 1820 (10) 1512-18 (2012) and Janko et al, *Lupus* 21(7):781-3 (2012). Elevated levels of a number of galectins, including gal-3, are associated with inflammation and fibroses encountered in wound healing and the like. Gal et al. *Acta. Hisochem. Cytochem.* 26:44(5); 191-9 (2011). Quite obviously, mediation of inflammatory and fibrotic pathways makes galectins critical elements of a wide variety of disease, injury and trauma related phenomena. In many cases, the presence of unwanted concentrations of galectins can aggravate a disease condition or trauma situation, or interfere with attempts to treat diseases, such as cancer or congestive heart failure. Among the family of galectins recognized as active in humans, galectin-1, galectin-3 and galectin-9 are of particular interest. As indicated above, these proteins are generally referred to, and referred to herein as, gal-1, gal-3 and gal-9. A wide variety of conditions in humans, ranging from problems in conceiving to asthma to chronic heart failure to viral infection to stroke and beyond are mediated or aggravated by higher than normal concentrations of galectins. Thus, among other galectins, gal-3 is particularly prominent in fibrosis, inflammation and cell proliferation, while gal-1 also plays a role in the immunosuppression required for a successful pregnancy. Gal-1 is also thought to be involved in the differentiation of nerve cells. Gal-9 has been shown to be involved in the control of lesions arising from immunoinflammatory diseases, and is generally implicated in inflammation—gal-9 apparently plays a role in eosinophil recruitment in inflammatory sites. It also appears to mediate apoptosis in certain activated cells. While the discussion herein is applicable to circulating active gal-1, gal-3 and gal-9, and galectins in general, where elevated circulating galectin levels are associated with disease or injury conditions, more has been elucidated about the role of gal-3 in disease and trauma progression than any of the other galectins, and so it is exemplified herein. More specifically, this invention focuses on the removal of active gal-3 from mammalian, particularly human, plasma. Gal-3 has been shown to be involved in a large number of biological processes, many of which are related to disease states of various kinds. Binding and blocking activity of gal-3 in the circulation, or removal of large amounts of gal-3 from circulation may therefore improve existing medical treatments, suppress and/or reduce inflammation and fibrosis resulting from others, and make it possible to intervene in various disease states not otherwise easily treated. The invention is equally applicable to the reduction in circulating levels of other active galectins to address conditions mediated by those galectins. By "active" galectins, what is referred to is biologically active molecules. As noted, for example, gal-3 can be active, that is, mediate mammalian responses to various traumas and conditions, as a monomer and as an oligomer. In any mammal, at any given time, significant amounts of gal-3 and other galectins are present in an inactive state—that is, they are either tissue bound or ligand bound in such fashion as to inhibit molecular interaction. While such galectins molecules may become active, and may be or become the target of removal by the invention disclosed herein, when monitoring patient conditions and controlling responses, the focus of the invention is a device suitable for the removal of active galectins from the blood stream. This invention makes use of plasmapheresis, sometimes referred to as Apheresis, and/or therapeutic plasma exchange, to control levels of gal-3, and more specifically biologically active galectin, in circulation. Whole blood is first separated into its cellular and plasma components. Plasma is then led through a fluid pathway and either intermixed with a gal-3 binding agent which can be separated from the plasma, or returned to the body with blocked inactivated gal-3, or led past a solid support which binds gal-3, the plasma being subsequently returned to the body with a reduced level of gal-3. Thus, this invention can be used to remove bound gal-3 as part of a strategy to reduce total gal-3 content. The focus, in this application, however, is to remove active or unbound gal-3 as a therapeutic measure.

Related Art

This application is related to U.S. patent application Ser. No. 13/153,648, filed Jun. 6, 2011. That application in turn claims priority benefit to U.S. Pat. No. 8,426,567 issued Apr. 23, 2013. The content of both these parent documents is expressly incorporated herein-by-reference. In U.S. patent application Ser. No. 13/153,648 (U.S. Patent Publication US-2011-0294755 A1) a method of treating cell proliferation conditions, inflammation and aggravated fibroses is disclosed which involves the administration of an agent that can bind circulating gal-3, such as modified citrus pectin, (MCP), a citrus pectin which has a reduced molecular weight of twenty thousand (20,000) Daltons or less, preferably ten thousand (10,000) Daltons or so. MCP is available commercially from EcoNugenics of Santa Rosa, Calif. and is discussed in U.S. Pat. Nos. 6,274,566 and 6,462,029.

Background of the Biology

Gal-3 is approximately 30 kDa and, like all galectins, contains a carbohydrate-recognition-binding domain (CRD) of about one hundred thirty (130) amino acids that enable the specific binding of β-galactosides. Gal-3 is encoded by a single gene, LGALS3, located on chromosome 14, locus q21-q22. This protein has been shown to be involved in a large number of biological processes. The list set forth herein is exemplary only as new situations and roles for gal-3 are continually being revealed. Among the biological processes at the cellular level that have been shown to be mediated, at least in part, by gal-3, are cell adhesion, cell migration, cell invasion, cell activation and chemoattraction, cell growth and differentiation, angiogenesis and apoptosis.

Given gal-3's broad biological functionality, it has been demonstrated to be involved in a large number of disease states or medical implications. Studies have also shown that the expression of gal-3 is implicated in a variety of processes associated with heart failure, including myofibroblast proliferation, fibrogenesis, tissue repair, inflammation, and ventricular and tissue remodeling. Elevated levels of gal-3 in the blood have been found to be significantly associated with increased morbidity and mortality. They have also been found to be significantly associated with higher risk of death in both acute decompensated heart failure and chronic heart failure populations.

Various investigations have shown elevated levels of gal-3 to aggravate a wide variety of disease conditions associated with cell proliferation. High levels of gal-3 are linked to cancer growth and cancer progression to a metastatic stage in a stunning variety of cancers. A number of cancers have been specifically linked to or associated with elevated gal-3 levels, including liver cancer, kidney cancer, breast cancer, prostate cancer, colon cancer, thyroid cancer, cancer of the gallbladder, nasopharyngeal cancer, lymphocytic leukemia, lung cancer, melanoma, multiple myeloma, glioblastoma multiforme, uterine cancer, ovarian cancer, cervical cancer, brain cancer and others. Elevated gal-3 levels have also been shown to interfere with or suppress conventional antineoplastic regimens, such as chemotherapeutic treatments like cisplatin, doxorubicin and related chemotherapeutics.

Inflammation is a commonly encountered body condition—a natural response of the body to a variety of diseases and trauma. As with the other conditions noted above, gal-3 levels above normal levels are implicated in a wide variety of situations where harmful inflammation is encountered. Again, the list of conditions and disease states is too extensive to exhaust every possibility, but inflammatory conditions associated with elevated gal-3 levels include aggravated inflammation associated with non-degradable pathogens, autoimmune reactions, allergies, ionizing radiation exposure, diabetes, heart disease and dysfunction, atherosclerosis, bronchial inflammation, intestinal ulcers, intestinal inflammation of the bowels, cirrhosis-associated hepatic inflammation, parasitic infection associated inflammation, inflammation associated with viral infection, inflammation associated with fungal infection, inflammation associated with bacterial infection, inflammation associated with infection by intracellular organisms and associated infections such as tuberculosis, sarcoidosis, cat scratch fever, mycoplasma, Lyme's disease, bartonellosis, ehrlichiosis, rickettsial diseases, babesiosis, and others. Inflammation associated with arthritis, with multiple sclerosis, psoriasis, Alzheimer's disease, Parkinson's disease, and amyotrophic lateral sclerosis (ALS) may also be addressed. Again, while inflammation is a pathway frequently employed by the body in responding to any number of challenges, elevated levels of gal-3 have been found to aggravate and promote the inflammation, causing damage and injury leading to morbidity or mortality in a wide variety of situations that am otherwise manageable, including inflammation due to heavy metal poisoning, pesticides, oxidative agents, xenoestrogens, and similar toxins, stroke and related ischemic injuries, liver inflammation due to acetaminophen, a number of T-cell mediated responses generally involved in autoimmune diseases and the like. Gal-3 is also involved with kidney injury and kidney disease, hepatitis, pulmonary hypertension and fibrosis, diabetes, and gastrointestinal inflammatory conditions such as ulcerative colitis, Crohn's disease, celiac disease, and others.

As noted, elevated levels of circulating, active gal-3 are associated with, and apparently promote, a number of inflammatory conditions, including those contributing to cardiovascular, kidney, lung, brain, and liver diseases. Gal-3 is also associated with a fibrotic formation, particularly in response to organ damage. Higher levels of circulating gal-3 are found to induce pathogenic fibroses in cardiovascular disease, gastroenterological disease, cardiovascular trauma, renal tissue trauma, brain trauma, lung trauma, hepatic tissue trauma, tissue damage due to radiation therapy and diseases and conditions of connective tissue and skin such as systemic sclerosis.

Accordingly, the art is replete with observations that elevated levels of gal-3, as well as gal-1 and gal-9, can complicate or exacerbate a wide variety of disease and injury conditions. It would be of value to find a way to control inflammation and formation of fibroses, where the inflammation and fibroses are injurious, particularly in the environments described above, and notably in cardiac care and other organ tissue disease and trauma. By the same token, it would be of value to control the cellular responses mediated by gal-3 that accelerate cell proliferation and transformation, including the formation and growth of tumors, the transformation of cancer cells and metastatic spread of cancer. Another goal in the art is to avoid the problem posed by the interference of elevated gal-3 levels in the treatment of cancer by conventional agents, like bleomycin, doxorubicin (Adriamycin) and other anthracyclines, cyclophosphamide and cyclosporine, as well as targeted biological agents such as VEGF and EGF inhibitors, examples being bevacizumab (Avastin) and erbitux (Cetuximab). Some of the side effects caused by these agents are gal-3 mediated, and can be addressed and ameliorated by the invention, while their mechanism of action can be blocked by gal-3 (enhancing angiogenesis). Elevated gal-3 levels also appear to interfere with pharmaceuticals used in other applications, such as the antiarrhythmic drug amiodarone (Cordarone), and statin drugs.

Plasmapheresis is a blood separation technology, where blood is diverted from the body through a needle or catheter to a separator which removes blood cells and returns them to the body, leaving plasma. Cells are returned to the body when plasma has been reunited with the cellular components or a replacement fluid has been added to the blood cells. This type of technique has been used historically in the treatment of autoimmune diseases, where the antibodies at issue are removed by contacting the plasma with the ligands to which they bind. The plasma is then augmented as required, with anticoagulants, therapeutics and associated elements, recombined with the blood cells and returned to the body. In prior art methods employing plasma exchange or replacement therapies generally, as illustrated in U.S. patent publication US 2006/0129082, the technology was used to target and remove "toxic serum components" such as ammonia, uric acid, and cell growth inhibitors. The same reference, at [0009]-[0010] warns against the use of plasma exchange in general. Similar warnings are sounded in Kyles et al, *Am. J. Crit. Care,* 14, 109-112 (2005) reviewing the use of plasmapheresis for support of immunoglobulin sepsis treatment, noting that traditionally, plasmapheresis has been used in treatments to remove pathogenic autoantibodies and endotoxins in autoimmune disorders and to remove harmful substances produced by the infecting organisms causing sepsis.

Background of Plasmapheresis Devices

An early form of apparatus for plasmapheresis is set forth in U.S. Pat. No. 3,625,212, which describes measures to ensure return of treated plasma, as well as the separated blood cells, to the proper donor. U.S. Pat. No. 4,531,932 addresses plasmapheresis by centrifugation, the method used to separate out the red blood cells, on a rapid and near-continuous basis. U.S. Pat. Nos. 6,245,038 and 6,627,151 each describe a variety of methods of separating out plasma contents and returning the treated plasma to the patient after first removing red blood cells, in general, to reduce blood viscosity by removal of high molecular weight protein. While the invention that is the subject of this application focuses on the reduction in galectins circulating levels, such as gal-3 levels, and not high molecular weight proteins or directly addressing viscosity, the disclosure of these four (4) patents is incorporated herein-by-reference for their disclosure of available plasmapheresis techniques and apparatus which may generally be employed in this invention. Advances in apheresis generally, including plasmapheresis, have demonstrated the effectiveness of the use of hemodialysis equipment using a highly permeable membrane like the Plasmaflo AP-05H from Asahi Medical and a standard dialysis machine in ultrafiltration mode. This is similar to hemoperfusion in application.

SUMMARY OF THE INVENTION

The plasmapheresis device of this invention advances the art by providing for the selective removal of gal-3 from the plasma that has been separated out of the whole blood of a mammal in need of active gal-3 reduction. As referenced in co-pending U.S. patent application Ser. No. 13/863,989 filed Sep. 28, 2012 and Ser. No. 14/141,509 filed Dec. 27, 2013 the removal of active gal-3 from the blood stream of a mammal may be effected to address unwarranted inflammation, to reduce the danger posed by fibrosis, particularly cardiac fibroses, to reduce the danger or spread of a variety of cancers, to enhance treatments, etc. The critical requirement of this plasmapheresis device, therefore, is the selective removal of gal-3. This is affected by directing separated plasma through a component that selectively binds gal-3. This may be a column, container, or similar platform in which a material which positively binds gal-3, such as an antibody thereto, is physically held, so that as the plasma passes through, a significant fraction of the gal-3 entrained therein is bound by the column. In other embodiments, the selective gal-3 removal is effected by combining the stream of plasma in the conduit of the machine with a material which binds to the gal-3, and then itself is easily removed, either by an antibody specific to it, or by secondary means, such as attached magnetic particles which can be drawn out by selective application of a magnetic charge.

The invention is not limited to the removal of gal-3, however. Ideal machines provide this selective removal capability with the capability to remove other components from the blood which may either mediate or reinforce disease conditions. As only one example of possible scenarios, the machine may be provided with multiple removal or absorption columns, with one removing gal-3, and a second removing TNFα and a third removing TGFβ, or the same column having multiple filters in sequential order to remove these three. Additional examples of compounds to be removed are C-reactive protein (CRP), fibrinogen, NFkβ, different inflammatory cytokines, etc. which may be implicated in a patient with chronic inflammation in a variety of disease states including cancer. Not only will treating the blood in the inventive device remove reinforcing inflammation response enhancers, but by doing so, and possibly removing receptors for these markers which block them—the effectiveness of antineoplastic medications or treatments can be enhanced. Thus, the device of the invention advantageously includes multiple columns or removal elements, for selectively removing not only gal-3, but other agents commonly found to be elevated in the blood of individuals with a variety of both chronic and acute conditions.

As also described in the priority cases though, effective treatment may depend not only on selective removal of gal-3 from the blood, and other blood agents, but it may depend on the addition of therapeutic or beneficial elements before the blood is returned to the mammal. Often, addition of the agent to the plasma is an effective and efficient means of administration of the treatment, such as a medication, vitamin, or similar component. Thus while not essential to the selective removal of gal-3, the inventive device of this invention includes multiple ports for the addition of a variety of agents to the plasma and coined whole blood. Examples include various homeopathic medications, metabolism regulators, immune reaction modifiers, pharmaceuticals and various cytotoxic compounds, anti microbial agents, chelating agents, possibly targeted ones, to aid in treatment.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE PREFERRED EMBODIMENTS

Description

Figure 1:
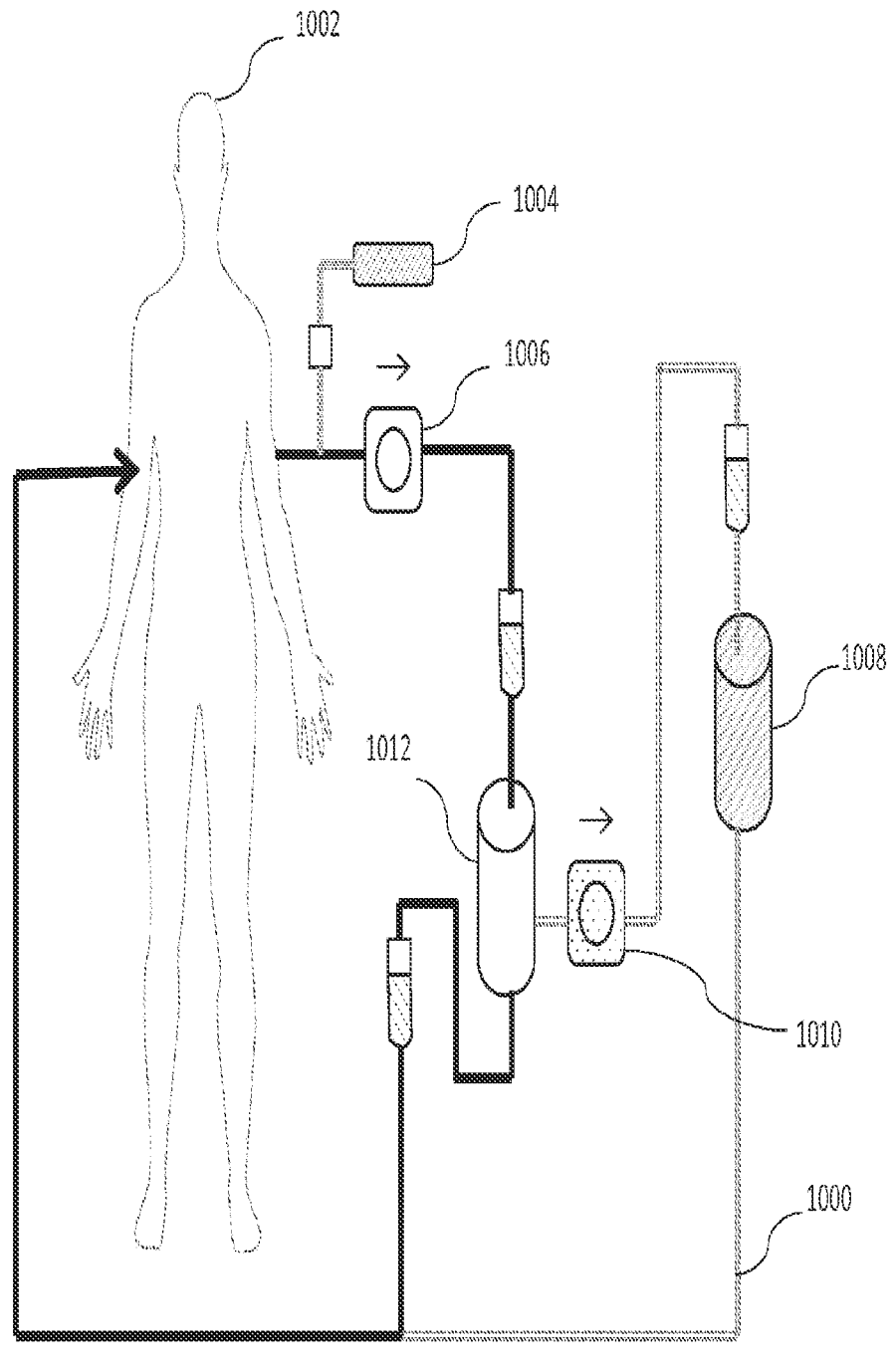
FIG. 1 is a broad schematic illustration of the device of this invention, reflecting separation of whole blood into blood and plasma, treatment of the plasma, return of the plasma to the blood component and restoration of the treated whole blood to the patient.

The plasmapheresis device of this invention is depicted generally in FIG. 1. Blood is withdrawn from mammalian patient 1002, typically through insertion of a venous catheter, either peripheral in a limb or central vein. Central veins allow higher flow rates and are more convenient for repeat procedures, but are more often the site of complications, especially bacterial infection. The catheter is not part of the inventive device, per se, and is typically provided by the operator, e.g., a clinic or hospital. The catheter is connected to the conduit of the device, 1000, and positive flow, assisted by pump 1006, distributes the blood through the system.

Once blood is being removed from the body of the patient per se, the plasmapheresis device begins in the normal method. Thus, as a first step in the use of the device, an anticoagulant, such as heparin or a non-natural substance, like acenocoumarol or phenindione is provided at portal 1004. The addition of an anti-coagulant effective to prevent clotting induced by flow through the conduit and return to the patient is essential. In many individuals, a portal will be provided between the addition of the anti-coagulant and the blood/plasma separation device 1012 will be of value as illustrated in FIG. 1, but is not essential.

To reduce viscosity and pressure, and make treatment practical and effective, cellular components such as red blood cells (erythrocytes), white blood cells (WBC), and platelets, are removed and separated from the plasma. This is affected at separation device 1012. The separation device may be any conventionally used. Centrifuge separation is an old process in the art. It may include discontinuous flow centrifugation where one venous catheter is used, and aliquots of blood, perhaps up to about 500 ml, are removed at a time and centrifuged to remove blood cells from the plasma. Continuous flow centrifugation is also known, which reduces the amount of blood out of the body at any given time, but requires the use of two venous lines. This is the more commonly used method, where blood is drawn out from one site and returned through another site, usually in two different limbs. The catheters used allow for reverse of the flow. Almost always, continuous flow is used, with only 180 ml of blood being outside the body (extracorporeal) at a given time. This procedure usually pulls out an average of 60 ml/minute of blood and can filter 1.5 times plasma volume in about 2 hours. Flow rate and plasma volume to be filtered can be adjusted based on the medical needs.

As an alternative to centrifugation, membrane plasma separation, using now-standard dialyzing membranes, may be gentler, but may increase the time spent in treatment.

As a general observation, support and supervision of the patient is required throughout the use of the inventive device. Though the device can be largely automated, this is not a device generally suitable for home or unsupervised use. To that end, an operator control station or interface is provided, which allows for directed control, as well as automation of virtually any function of the device, including levels of agents such as anticoagulant added, speed of transport, type of column, port sampling and the like. It is practical and possible to continuously monitor a wide variety of mammalian indications using the device, and sampling ports are provided to that end. Part of the operating platform may include a monitor that checks pulse rate, oxygen saturation, basic ECG rhythm, and blood pressure.

At separation unit 1012, the stream removed from mammalian patient 1002 is split, with red blood cells and other cellular components supported in fluid being directed on to return. Prior to return, one or more ports are typically provided in this line. There may be a variety of reasons for removing cells at this point. This can be combined with the plasma separation device, but ports are provided for removing various cells in addition to separating the blood cells, including cells such as stem cells, T cells, B cells, NK cells, etc. There is more opportunity for capture of various cells from the plasma and use or return, but this operation can be combined with, and integrated into, plasma separation unit 1012.

The plasma from the separator is driven by pump 1010 through at least one column 1008. Column 1008 contains, as described above, one or more elements that selectively bind or remove gal-3 from the plasma. In the most traditional format, the "column" is a tube which is lined with a physically fixed binding agent, such as an antibody bound to the interior wall of the tube through an agent like sepharose, but a wide variety of antibody-binding proteins, compatible with in vitro plasma passage are well known, including Protein A, Protein G, and Protein L. Other binders such as negatively charged compounds, resins, glycoproteins, etc. can be used. As the plasma passes through the conduit, it necessarily 'bathes' the binding moieties which selectively remove a percentage of gal-3 from the plasma. The columns may be of any variety known, and as indicated above, may in fact not be "traditional columns" (such as spin columns) but may in fact be open passages where gal-3 is selectively bound by modified particles, such as particles of pectin which are biologically compatible or the galectin binding molecule, N-acetyl-lactosamine, or modified pectin such as citrus pectin. These particles are typically modified to include an element which makes their fixation and/or removal straightforward, such as a magnetically attractable particle to be bound by a suitable magnet. The nature of the column is not particularly limited, save that it must selectively bind gal-3. Size and number of the columns will vary, and ideally, the device of the invention can accommodate a different number of columns based on the needs of the patient. One column may be effective in removing, for example, 10% or more of the active gal-3 in the patient's circulation. While ten percent will be effective to produce therapeutic effects in many patients, in some patients, depending on the nature of the selection criteria, including, e.g., selection for relief from inflammation as opposed to inhibition of the spread of metastatic cancer, more removal may be required. To this end, the device of the invention may be provided with multiple columns 1008. Thus, use of the device may be effective in removing fifteen percent, twenty percent, or even more, on up to perhaps forty percent of circulating gal-3. The amount of gal-3 selectively removed by column(s) 1008 is effectively limited by the flow dynamics of the system, binding affinities of materials, and the needs of the patient. Regeneration columns can be put in place parallel to one another so one can be regenerated or cleaned and the machine can switch between them automatically at certain plasma volume intervals. Associated features commonly employed in the art of plasmapheresis include pressure lines for the whole blood, the plasma, and for columns with each having pressure filters and pressure monitoring lines. Separate pumps are needed for whole blood, and then for the plasma flow route, and then also for certain types of columns, such as double regeneration adsorption columns, since they flush and clean out and alternate back and forth, they need their own pump. Also commonly employed are air detectors, blood leakage detectors, conductivity detectors, blood warmers, waste bags/lines, etc. and input lines for fluid for column regeneration. These are collectively referred to herein as column support elements.

Following plasma treatment including the selective removal of gal-3, the plasma flow is recombined with the cellular components (RBC, WBC, platelets) flow and the recombined blood is returned to the patient. Often, some level of augmentation, using synthetic plasma, albumin, auxiliary blood cells, and sometimes saline solution, are used to ease flow return by addition through ports to the device conduits. Speeds and pressures observed are conventional. Accordingly, treatment may include several hours where the patient is connected to the machine. Effective treatment depends on a wide variety of factors including those of the patient and the capacity of the machine itself. Oftentimes treatment occurs more than once a week, and in acute cases, more than once a day. Gal-3 concentration, as well as the concentration of other agents targeted for the patient in question, is monitored, both in the returned plasma/blood, and in the blood being withdrawn, to allow monitoring and equilibration. When active gal-3 levels have been reduced to a beneficial level, the withdrawal of blood is ended, and on return of the last plasma/blood to the patient, the treatment is over.

Figure 2:
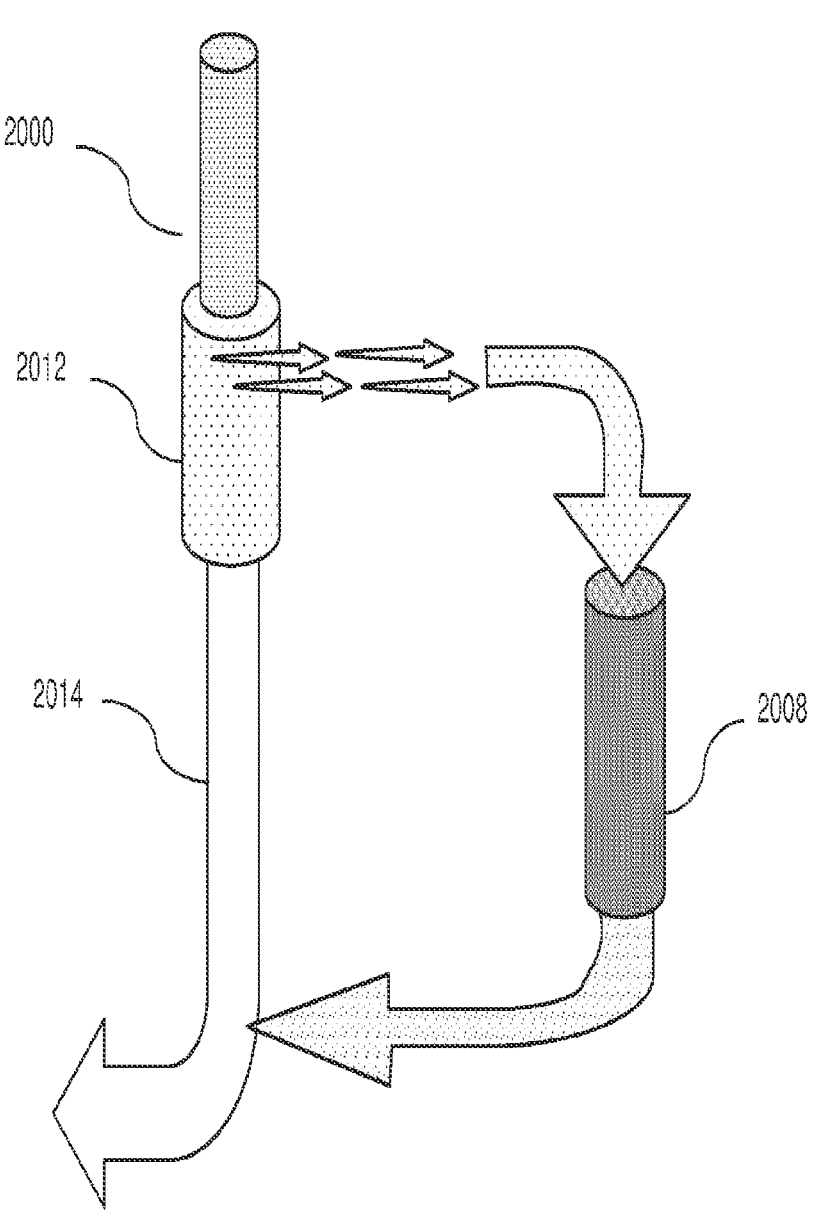
FIG. 2 is an illustration schematic of the portion of the device where plasma is separated out of the blood, (which can occur via one of several existing separation technologies) treated in at least one column and returned via a conduit to the blood and donor.

FIG. 2 reflects the "plasma lop" of the device. As shown, the whole blood removed from the patient is entrained in conduit 2000, after the addition of anticoagulant. In FIG. 2, blood/plasma separation occurs at separation device 2012, which is optionally a membrane separation device, where passage is permissive based on size. Plasma is shunted in the direction of the arrows as shown, while the red blood cells and other cellular components continue on through conduit 2000. The principal feature of this loop is "column" 2008. The column need not be a traditional column. Hollow glass fiber filter technology is widely available. A representative product is that offered by Calux of China, but numerous providers are well known. What is novel and different about this "column" is its selective removal of gal-3.

Clearly, a patient whose condition could be improved by plasmapheresis would most likely obtain added therapeutic benefit from removal of other abnormally elevated or potentially harmful substances or agents found in the plasma, and so more than one "column" 2008 may be used. The device of this invention may provide for multiple filters to be rotated in or out as a "cassette" in preferred embodiments. Among potential targets for joint removal together with the selective removal of gal-3 may be heavy metals (e.g., mercury), antibodies such as dangerous autoantibodies, pesticides and toxins, LDLs, Lp-PLA-2, LP(a), oxidized cholesterol, oxidized LDL, cytokines (examples such as IL-6, IL-8), immunoglobulins of various types, complement, CRP, TNFα, receptors for TNFα, TGFβ, NFkβ, growth factors such as VEGF, other inflammatory components such as CRP, fibrinogen, heavy metals binding proteins such as ceruloplasmin for copper, other galectins (in particular galectins-1 and 9) and cytokine receptors such as IL-2 receptors, TNF-α receptors, etc. Accordingly, provided selective removal of gal-3 is provided for at the beginning, middle or end of the plasma treatment loop, other elements may be removed using columns specific for their removal.

Figure 3:
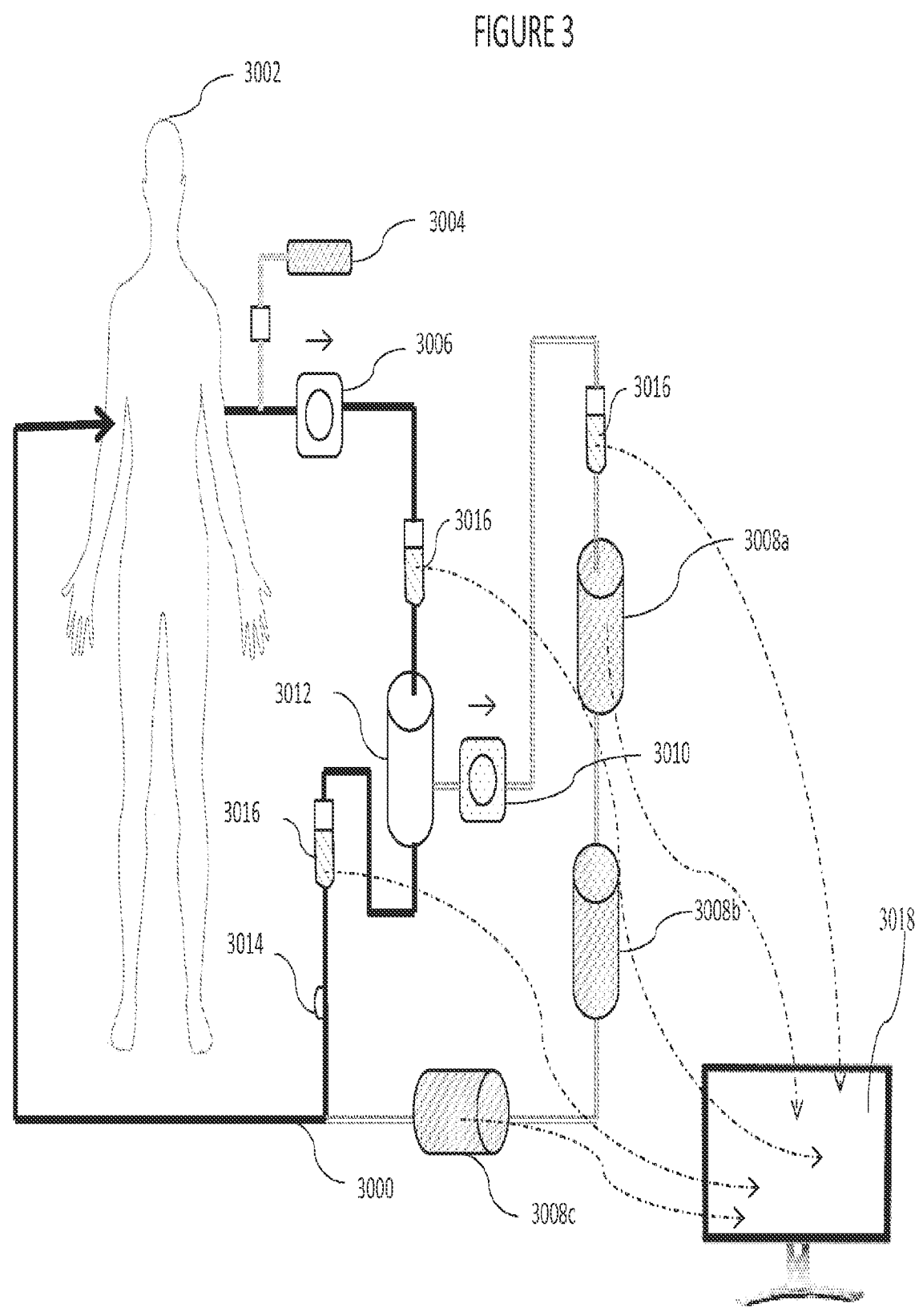
FIG. 3 is a schematic of the inventive device deliberately echoing the structure of FIG. 1, but reflecting the ability of this device to introduce multiple columns and ports to both remove and add a variety of components to the plasma and ultimately the patient.

As noted, in addition to the value of removal of gal-3, the claimed device may advantageously provide for the addition of various agents prior to reintroduction of blood to the patient. The additions described above, as well as other pharmaceuticals, are contemplated. As one particular illustration, the incorporated disclosure makes it clear that removal of a certain amount of circulating gal-3 may enhance the effectiveness of certain antineoplastic pharmaceuticals. To maximize that enhancement, the pharmaceutical might be advantageously added to the plasma or the reunited bloodstream prior to return to the patient, thus being added at a time when gal-3 levels in the patient are likely to be lowest. An optimized device is illustrated in FIG. 3, so that the artisan can compare the simplified device with the description set forth above. Blood from patient 3002 again flows through conduit 3000 where anti-coagulant is added to prevent clotting ex vivo as well as following reintroduction to the patient. Anticoagulant is added at 3004, after which the blood flows through pump 3006 past a port 3016. Multiple ports 3016 are included in the conduits through which blood, red blood cells and plasma flow. Three ports are illustrated, but in fact the device may include as many as are appropriate to the purpose, and typically will include more. Six may be a more realistic value, but the ports may be used to both withdraw fluid and to add the elements discussed above. In preferred embodiments, operation of the ports, including withdrawal and addition, is carried out by the automated device control system, with operations having been preselected by the operator, with the option for manual operation as needed. Advantageously, ports are provided in the line where the patient's blood is withdrawn, the plasma line, the red blood cell line after separation, and in the recombined line prior to reintroduction to the patient, but the placement and selection of the ports will vary from machine to machine.

In addition to the removal and addition of the various elements discussed above, the device described permits the use of separators such as separator 3012 to 'harvest' a variety of cells for treatment or use, such as B cells, T cells, platelets, stem cells and the like. Many of these cells and fragments are usefully banked for later treatment of the patient. Advantageously, the cells may be withdrawn and modified and returned with the same device an example being T cells or B cell Lymphocytes being treated to be able to recognize cancer cells of a specific type in a specific patient, and attack them. When reintroduced into this device while gal-3 and other inflammatory mediators are reduced, the antineoplastic effect can be enhanced while avoiding the dangerous, and often life threatening inflammatory response. Various enhancement therapies, such as circulating tumor cell (CTC) therapy are best taken advantage of through this type of device. Among a variety of advantages, simplifying patient sampling, reducing the possibility of infection, and improving monitoring and control am affected by using this machine. In CTC, tumor cells are removed from the separated plasma at the separator. These cells, which are effectively metastatic tumor emboli, are modified to carry antibodies and/or viruses, and returned to the body. They effectively become targeted killing cells, which the body recognizes and does not attack. They can also be used to create antibodies that are then reintroduced to the body and attack any cancer present in the patient, or lymphocytes harvested from the cancer patient are sensitized against certain surface membrane proteins specific to the patient's cancer cells, and then returned. Performing such procedures under reduced inflammatory burden reduces the side effects and can enhance the effectiveness of such therapies.

Each plasmapheresis device may be optimized in different fashion, but the device illustrated in FIG. 3 includes three different columns 3008*a-c*. These are identified separately. While one of these will selectively remove gal-3 as discussed above, the remaining two, in any order, may selectively remove other components whose removal may provide therapeutic benefit. Each of these columns 3008 will be provided with its own support elements. Related support elements 3014 may be distributed throughout the conduit passage of the plasmapheresis device. As noted above, removal and addition of various factors, as well as sampling, will occur in most devices. This is most easily effected through discreet support elements 3014, which may be combined with columns 3008 or separately, as shown in FIG. 3.

Monitoring may be effected by an operator at control interface 3018, which as shown is in effective communication with the devices and ports described above. Communication may be hardwired, in a fashion similar to devices for surgical manipulation like the DaVinci® device, or be remote and achieved via blue-tooth or internet means. Computer control through interface 3018, which conventionally includes a visual monitor that may display a variety of relevant data, permits pre-programmed operation of much of the plasmapheresis device of this invention, and the use of alarms and similar methods to alert the operator to situations arising outside of "normal" parameters. Advantageously, through servomotor control, the operator, either through preprogrammed operations, or directly, may effect column change, flow modification, port opening and closing, withdrawal and addition, without need for additional individuals. This not only limits the cost and time of treatment, but reduces complexity and limits infection risk.

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A device for performing plasmapheresis, comprising:
   a first conduit through which blood drawn from a mammalian patient travels under the influence of a pump;
   a separator for separating cellular components of said blood from plasma;
   a column device through which said plasma flows, which said column device selectively removes a plasma component, wherein said plasma component is selected from the group consisting of low-density lipoprotein, lipoprotein-associated phospholipase A2 and lipoprotein A,
   a second column device for selective withdrawal of galectin-3 from said plasma, wherein said plasma encounters said first column device and second column device in any order,
   a second conduit which receives said treated plasma following passage in said column devices and wherein said treated plasma is combined with blood cells separated in said separator prior to return to said mammalian patient;
   wherein said first and second conduits provide for continuous flow of said blood and plasma from said patient and return to said mammalian patient.

\* \* \* \* \*